United States Patent [19]

Kim

[11] Patent Number: 5,225,203

[45] Date of Patent: Jul. 6, 1993

US005225203A

[54] PHARMACEUTICAL LIQUID COMPOSITION CONTAINING BEZOAR BOVIS

[76] Inventor: Young S. Kim, Cosmos Mansion 1002, #302-62 Ichon-Dong, Yongsan-Ku, Seoul, Rep. of Korea

[21] Appl. No.: 878,215

[22] Filed: May 4, 1992

Related U.S. Application Data

[63] Continuation-in-part of Ser. No. 595,671, Oct. 11, 1990, Pat. No. 5,133,964, which is a continuation of Ser. No. 171,432, Mar. 21, 1988, abandoned.

[30] Foreign Application Priority Data

Jul. 1, 1987 [KR] Rep. of Korea ............... 87-6998

[51] Int. Cl.$^5$ ............................................. A61K 35/78
[52] U.S. Cl. ................................. 424/195.1; 424/520; 424/551
[58] Field of Search ................. 424/195.1, 520, 551

[56] References Cited

PUBLICATIONS

Joon Huh, Annals of Oriental Medicine.

Primary Examiner—John W. Rollins
Attorney, Agent, or Firm—Birch, Stewart, Kolasch & Birch

[57] ABSTRACT

A pharmaceutical liquid composition such as suspension, gel, or sol preparation, contains *Bezoar Bovis, Dioscoreae Rhizoma, Glycyrrhizae Radix, Ginseng Radix, Typhae Pollen, Massa Medicata Fermentata, Sojae germinatum Semen, Cinnamomi Cortex,* Gelatin, *Paeoniae Radix Liriopis Tuber, Scutellariae Radix, Angelicae Gigantis Radix, Ledebouriellae Radix, Atractylodis Rhizoma Alba, Bupleuri Radix, Platycodi Radix, Armeniacae Semen,* Hoelen, *Cnidii Rhizoma, Antellopis Cornu,* Moschus, Borneol, *Ampelopsis Radix,* and *Zingiberis Rhizoma* for easy oral and parental administration thereof to critical patients.

6 Claims, No Drawings

PHARMACEUTICAL LIQUID COMPOSITION CONTAINING BEZOAR BOVIS

CROSS-REFERENCE TO RELATED APPLICATION

This is a Continuation-in-part application of copending U.S. patent application Ser. No. 07/595,671, filed on Oct. 11, 1990, now U.S. Pat. No. 5,133,964 which in turn is a continuation application of U.S. patent application Ser. No. 07/171,432, filed on Mar. 21, 1988, now abandoned.

BACKGROUND OF THE INVENTION

1. Field of the Invention

The present invention relates to a novel pharmaceutical liquid composition containing *Bezoar Bovis* for treating patients suffering from stroke, arteriosclerosis, hypertension, tachycardia, dyspnea, anxiety, cardiostenosis, acute and chronic convulsion, automatic nervous system disease, and coma. More particularly, the present invention relates to the preparation of oral and parental natural substance liquids of improved physical stability.

2. Description of the Prior Art

The solid pills containing *Bezoar Bovis* are known in the art. Such solid pill containing *Bezoar Bovis*, which contains 45 mg of *Bezoar Bovis*, 263 mg of *Dioscoreae Rhizoma*, 188 mg of *Glycyrrhizae Radix*, 94 mg of *Ginseng Radix*, 94 mg of *Typhae Pollen*, 94 mg of *Massa Medicata Fermentata*, 66 mg of *Sojae germinatum Semen*, 66 mg of *Cinnamomi Cortex*, 66 mg of Gelatin, 56 mg of *Paeoniae Radix*, 56 mg of *Liriope Tuber*, 56 mg of *Scutellariae Radix*, 56 mg of *Angelicae Gigantis Radix*, 56 mg of *Ledebouriellae Radix*, 56 mg of *Atractylodis Rhizoma Alba*, 47 mg of *Bupleuri Radix*, 47 mg of *Platycodi Radix*, 47 mg of *Armeniacae Semen*, 47 mg Hoelen, 47 mg of *Cnidii Rhizoma*, 38 mg of *Antellopis Cornu*, 38 mg of *Moschus*, 38 mg of *Borneol*, 28 mg of *Ampelopsis Radix*, and 28 mg of *Zingiberis Rhizoma*. However, such prior art *Bezoar Bovis* pills suffer from a many disadvantages such as, for example, it is not feasible for patients in critical condition to orally and parentally administer this pill nor for infants and children to orally and parentally administer them. Furthermore, this pills do not provide for treatment of the illness of a patient in a fast manner.

SUMMARY OF THE INVENTION

Accordingly, it is an object of the present invention to provide a pharmaceutical liquid composition such as suspension, gel, or sol preparation which is a mixture of natural substances including *Bezoar Bovis*, *Dioscoreae Rhizoma*, *Glycyrrhizae Radix*, *Ginseng Radix*, *Typhae Pollen*, *Massa Medicata Fermentata*, *Sojae germinatum Semen*, *Cinnamomi Cortex*, Gelatin, *Paeoniae Radix*, *Liriopis Tuber*, *scutellariae Radix*, *Angelicae Gigantis Radix*, *Ledebouriellae Radix*, *Atractylodis Rhizoma Alba*, *Bupleuri Radix*, *Platycodi Radix* *Armeniacae Semen*, Hoelen, *Cnidii Rhizoma*, *Antellopis Cornu*, *Moschus*, *Borneol*, *Ampelopsis Radix*, and *Zingiberis Rhizoma* for easy oral and parental administration thereof to critical patients.

Another object of the present invention is to provide a pharmaceutical liquid preparation from the above-identified natural substances for providing medication to infants and children.

A further object of the present invention is to provide a preparation method for manufacturing a pharmaceutical liquid composition containing ox *Bezoar Bovis* for cleaning a patient's chest.

Other objects and further scope of applicability of the present invention will become apparent from the detailed description given hereinafter. It should be understood, however, that the detailed description and specific examples, while indicating preferred embodiments of the invention, are given by way of illustration only, since various changes and modifications within the spirit and scope of the invention will become apparent to those skilled in the art from this detailed description.

The present invention pertains to a pharmaceutical liquid composition containing *Dioscoreae Rhizoma*, *Glycyrrhizae Radix*, *Ginseng Radix*, *Typhae Pollen*, *Massa Medicata Fermentata*, *Sojae germinatum Semen*, *Cinnamomi Cortex*, *Paeoniae Radix*, *Liriopis Tuber*, *Scutellariae Radix*, *Angelicae Gigantis Radix*, *Ledebouriellae Radix*, *Atractylodis Rhizoma Alba*, *Bupleuri Radix*, *Platycodi Radix*, *Armeniacae Semen*, Hoelen, *Cnidii Rhizoma*, *Antellopis Cornu*, *Ampelopsis Radix*, *Zingiberis Rhizoma*, *Bezoar Bovis*, Moschus, Borneol, and Gelatin with water or alcohol for orally administering to patients such as infants, children, critical patients, and the like.

DESCRIPTION OF THE PREFERRED EMBODIMENTS

Referring now in detail to the present invention, there is provided a pharmaceutical liquid composition *Bezoar Bovis*, *Dioscoreae Rhizoma*, *Glycyrrhizae Radix*, *Ginseng Radix*, *Typhae Pollen*, *Massa Medicata Fermentata*, *Sojae germinatum Semen*, *Cinnamomi Cortex*, Gelatin, *Paeoniae Radix*, *Liriopis Tuber*, *Scutellariae Radix*, *Angelicae Gigantis Radix*, *Ledebouriellae Radix*, *Atractylodis Rhizoma Alba*, *Bupleuri Radix*, *Platycodi Radix*, *Armeniacae Semen*, Hoelen, *Cnidii Rhizoma*, *Antellopis Cornu*, Moschus, Borneol, *Ampelopsis Radix*, and *Zingiberis Rhizoma*. Before the cutting or extracting the natural substances, the genera *Bezoar Bovis*, *Dioscoreae Rhizoma* *Glycyrrhizae Radix*, *Ginseng Radix*, *Typhae Pollen*, *Massa Medicata Fermentata*, *Sojae germinatum Semen*, *Cinnamomi Cortex*, Gelatin, *Paeoniae Radix*, *Liriopis Tuber*, *Scutellariae Radix*, *Angelicae Gigantis Radix*, *Ledebouriellae Radix*, *Atractylodis Rhizoma Alba*, *Bupleuri Radix*, *Platycodi Radix*, *Armeniacae Semen*, Hoelen, *Cnidii Rhizoma*, *Antellopis Cornu*, Moschus, Borneol, *Ampelopsis Radix*, and *Zingiberis Rhizoma* are mixed together in a predetermined weight ratio. First of all, 263 g of *Dioscoreae Rhizoma*; 188 g of *Glycyrrhizae Radix*; 94 g of *Ginseng Radix*, *Typhae Pollen*, and *Massa Medicata Fermentata*; 66 g of *Sojae germinatum Semen* and *Cinnamomi Cortex*; 56 g of *Paeoniae Radix*, *Liriopis Tuber*, *Scutellariae Radix*, *Angelicae Gigantis Radix*, *Ledebouriellae Radix*, and *Atractylodis Rhizoma Alba*; 47 g of *Bupleuri Radix*, *Platycodi Radix*, *Armeniacae Semen*, Hoelen, and *Cnidii Rhizoma*; 38 g of *Antellopis Cornu*; and 28 g of *Ampelopsis Radix* and *Zingiberis Rhizoma* are cut into microparticle size or extracted with water or alcohol to form a first microparticle product or extract. Secondly, 45 g of *Bezoar Bovis* and 38 g of Moschus are cut into microparticle size to produce a second microparticle product and then water is added to the second microparticle product to produce *Bezoar Bovis* solution, and Borneol is mixed with ethanol to produce Borneol solution. Thirdly, 66 g of Gelatin is added to distilled water at an elevated temperature to produce a Gelatin solution.

The above-produced first microparticle product or extract, *Bezoar Bovis*, Borneol, and Gelatin solutions are then mixed together with water or alcohol to produce a pharmaceutical liquid composition for orally administering to patients. At this time, if necessary, a preservative, sweetening agent, stabilizer, solvent, emulsifier, colloidifier, aromatic agent, or the like can be added and mixed with the above-resulted liquid composition.

The species of the genera of natural substances found to be useful for the pharmaceutical composition of the present invention are Box taurus var domesticus Gmelin of *Bezoar Bovis*, *Glycyrrhiza glabra Linne* var *grandifera* or *Glycyrrhiza uratensis* of Glycyrrhizae Radix, Panax schinseng Nees of *Ginseng Radix*, *Typhar orientalis presl* of *Typhae Pollen*, *Glycine max Merril* of *Sojae germinatum Semen*, *Cinnamomum Cassia* of *Cinnamomi Cortex*, *Paeonia albiflora pallas* var. *trichocarpa* of *Paeoniae Radix*, *Liriope platyphylla Wang et Tang* of *Liriopis Tuber*, *Scutellaria baicalensis Georgi* of *Scutellariae Radix*, *Angelica gigas Nakai* of *Angelicae Gigantis Radix*, *Ledebouriella seseloides Wolff* of *Ledebouriellae Radix*, *Atractylodes japonica Koidzumi* of *Atractylodis Rhizoma Alba*, *Bupleurm falcatum Linne* of *Bupleuri Radix*, *Platycodon grandiflorum A de Candolle* of *Platycodi Radix*, *Prunus armeniaca Linne* var. *ansu Maximowicz* or *P. mandshurica Kochne* var. *glabra Nakai* of *Armeniacae Semen*, *Poria cocos Wolf* of Hoelen, *Cnidium officinale Makino* of *Cnidii Rhizoma*, *Gazella subgutturosa Guldenstaedt* of *Antellopis Cornu*, *Moschus moschiferus Linne* of Moschus, *Dryobalanops aromatica Gaertner* of Borneol, *Ampelopsis japonica Makino* of *Ampelopsis Radix*, *Zingiber officinale Roscoe* of *Zingiberis Rhizoma*, and *Dioscorea japonica Thumberg* of *Dioscoreae Rhizoma*.

Preservatives useful according to the present invention include p-oxybenzoic propyl (propyl-p-ben), p-oxybenzoic methyl (methyl-p-ben), sodium phosphoric benzoate, and the like.

Sweetening agents useful in accordance with the present invention include honey, sugar sorbitol, saccharine, ASPARTAME, and the like.

Solvents useful for the present invention include distilled water, ethanol, and the like.

Colloidal agents and emulsifiers which may be used include sodium carboxymethylcellulose, pectin, agar, sodium alginate, and the like. Useful aromatic agents include menthol, cinnamomi cortex, orange perfume, and the like. The present invention will now be described in more detail in connection with the following examples which should be considered as being exemplary and not limiting the present invention.

EXAMPLE 1

263 g of *Dioscoreae Rhizoma*; 188 g of *Glycyrrhizae Radix*; 94 g of *Ginseng Radix*, *Typhae Pollen*, and Massa Medicata Fermentata; 66 g of *Sojae germinatum Semen* and *Cinnamomi Cortex*; 56 g of *Paeoniae Radix*, *Liriopis Tuber*, *Scutellariae Radix*, *Angelicae Gigantis Radix*, *Ledebouriellae Radix*, and *Atractylodis Rhizoma Alba*; 47 g of *Bupleuri Radix*, *Platycodi Radix*, *Armeniacae Semen*, Hoelen, and *Cnidii Rhizoma*; 38 g of *Antellopis Cornu*; and 28 g of *Ampelopsis Radix* and *Zingiberis Rhizoma*, are cut into microparticle size by a cutting apparatus. Then 7.5 liters of water are added to approximately 1.5 Kg of the natural substance mixture in an extractor. The mixture in the extractor is stirred and condensed. Thereafter, the aqueous mixture is filtered and residues from the first filtration are again filtered. Both filtrates are condensed for about 2 hours to produce a main natural substance extract.

45 g of *Bezoar Bovis* and 38 g of Moschus and 300 g of carboxymethylcellulose are ground into microparticle size in a grinder to form a microparticle mixture. Then 1 l of water is added to the microparticle mixture to produce a *Bezoar Bovis* solution.

10 Kg of sugar and 1 Kg of sorbitol or 1 Kg of ASPARTAME are dissolved in sufficient distilled water to make a sweetening solution which is added to the *Bezoar Bovis* solution to produce a sweetening *Bezoar Bovis* solution.

100ml of distilled water is added to 66 g of Gelatin and the aqueous mixture is heated to produce a Gelatin solution.

Sufficient ethanol and 5 g of 1-menthol are added to 38 g of Borneol to produce a Borneol solution.

The above-produced products, that is the main natural substance extract, the sweetening *Bezoar Bovis* solution, the Gelatin solution, and Borneol solution are mixed together with sufficient distilled water to abe a 30 l volume. Thereafter, the mixture solutio is stirred uniformly to produce a pharmaceutical liquid product for orally and parentally administering to patients. The final pharmaceutical liquid product can be prepared as a suspension or a gel, or the like so as to easily administrate.

EXAMPLE 2

The pre-extraction procedures in forming the natural substance mixture in Example 1 are repeated. The 7.5 l of ethanol are added to the natural substance mixture at a cold temperature and the extract are stored for about 10 days. The mixture is filtered and sufficient distilled water is added to the filtrate to make a natural substance extract.

The procedures for making the second Bezoar Bovis mixtures and the Gelatin solution of Example 1 are repeated. The main natural substance extract, *Bezoar Bovis* solution, Gelatin solution, Borneol solution are mixed and added to 30 liters of purified water for use as a pharmaceutical liquid.

EXAMPLE 3

263 g of *Dioscoreae Rhizoma*; 188 g of *Glycyrrhizae Radix*; 94 g of *Ginseng Radix*, *Typhae Pollen*, and *Massa Medicata Fermentata*; 66 g of *Sojae germinatum Semen* and *Cinnamomi Cortex*; 56 g of Paeoniae Radix, Liriopis Tuber, Scutellariae Radix, Angelicae Gigantis Radix, Ledebouriellae Radix, and *Atractylodis Rhizoma Alba*; 47 g of Bupleuri Radix, Platycodi Radix, Armeniacae Semen, Hoelen, and *Cnidii Rhizoma*; 38 g of *Antellopis Cornu*; and 28 g of *Ampelopsis Radix* and *Zingiberis Rhizoma*, are cut into microparticle size by a cutting apparatus to produce a main natural substance powder.

45 g of *Bezoar Bovis* and 38 g of Moschus and 300 g of carboxymethylcellulose are ground into microparticle size in a grinder to form a microparticle mixture. Then 1 l of water is added to the microparticle mixture to produce a *Bezoar Bovis* solution.

10 Kg of sugar and 1 Kg of sorbitol or 1 Kg of ASPARTAME are dissolved in sufficient distilled water to make a sweetening solution which is added to the Bezoar Bovis solution to produce a sweetening *Bezoar Bovis* solution.

100 ml of distilled water is added to 66 g of Gelatin and the aqueous mixture is heated to produce a Gelatin solution.

Sufficient ethanol and 5 g of 1-menthol are added to 38 g of Borneol to produce a Borneol solution.

The above-produced products, that is the main natural substance powder, the sweetening *Bezoar Bovis* solution, the Gelatin solution, and Borneol solution are mixed together with sufficient distilled ,water to abe a 30 l volume. Thereafter, the mixture solution is stirred uniformly to produce a pharmaceutical liquid product for orally and parentally administering to patients. The final pharmaceutical liquid product can be prepared as a suspension or a gel, or the like so as to easily administrate.

EXPERIMENT 1

The present Experiment 1 is the data resulting from experimentation of the pharmaceutical liquid according to the present invention. A 30 ml sample prepared from Example 1 is used in the following tests for determining the respective amount os (a) active bilirubin at a temperature of 30° C. and 60° C. (Table I), (b) active bilirubin in direct sunlight and in a room wherein the sun rays are scattered (Table 2), and active bilirubin after a long period of storage (Table 3) as follows:

TABLE 1

| | | | 30° C. | | | | | 60° C. | | | |
|---|---|---|---|---|---|---|---|---|---|---|---|
| | | Result | pH | Density | Viscosity | Content | Result | pH | Density | Viscosity | Content |
| Su-83001 | Beginning | Suitability | 4.819 | 1.130 | 20.62 | 189.6 | Suitability | 4.819 | 1.103 | 20.61 | 189.6 |
| | 2 (Months) | Suitability | 4.818 | 1.131 | 20.61 | 190.1 | Suitability | 4.819 | 1.131 | 20.54 | 189.6 |
| | 4 (Months) | Suitability | 4.817 | 1.130 | 20.64 | 188.6 | Suitability | 4.818 | 1.132 | 20.55 | 188.4 |
| | 6 (Months) | Suitability | 4.816 | 1.132 | 20.65 | 188.2 | Suitability | 4.816 | 1.131 | 20.57 | 187.0 |
| Su-83001 | Beginning | Suitability | 4.821 | 1.130 | 20.52 | 189.8 | Suitability | 4.821 | 1.130 | 20.52 | 189.8 |
| | 2 (Months) | Suitability | 4.820 | 1.130 | 20.55 | 189.3 | Suitability | 4.822 | 1.128 | 20.55 | 190.1 |
| | 4 (Months) | Suitability | 4.818 | 1.131 | 20.56 | 189.2 | Suitability | 4.186 | 1.131 | 20.35 | 188.2 |
| | 6 (Months) | Suitability | 4.819 | 1.131 | 20.58 | 187.4 | Suitability | 4.818 | 1.131 | 20.57 | 188.3 |
| Su-83003 | Beginning | Suitability | 4.817 | 1.131 | 20.63 | 190.2 | Suitability | 4.817 | 1.131 | 20.63 | 190.2 |
| | 2 (Months) | Suitability | 4.819 | 1.132 | 20.63 | 190.2 | Suitability | 4.817 | 1.130 | 20.52 | 188.4 |
| | 4 (Months) | Suitability | 4.817 | 1.131 | 20.65 | 190.0 | Suitability | 4.818 | 1.132 | 20.56 | 187.9 |
| | 6 (Months) | Suitability | 4.816 | 1.132 | 20.66 | 187.8 | Suitability | 4.816 | 1.132 | 20.58 | 186.9 |

TABLE 2

| | | Lot No. | | | | | | | | | | | | | |
|---|---|---|---|---|---|---|---|---|---|---|---|---|---|---|---|
| | | SU-83001 | | | | | SU-83002 | | | | | SU-83003 | | | |
| | | | | | | | Remarks | | | | | | | | |
| Condition | Period | Result | pH | Density | Viscosity | Content | Result | pH | Density | Viscosity | Content | Result | pH | Density | Viscosity | Content |
| Direct Ray | Beginning | Suitability | 4.819 | 1.130 | 20.62 | 189.6 | Suitability | 4.821 | 1.130 | 20.52 | 189.8 | Suitability | 4.817 | 1.131 | 20.63 | 190.2 |
| | 1 Day | Suitability | 4.821 | 1.130 | 20.63 | 188.2 | Suitability | 4.818 | 1.132 | 20.49 | 190.4 | Suitability | 4.823 | 1.131 | 20.55 | 190.2 |
| | 3 Days | Suitability | 4.817 | 1.131 | 20.61 | 188.9 | Suitability | 4.820 | 1.131 | 20.52 | 188.4 | Suitability | 4.818 | 1.132 | 20.64 | 189.1 |
| | 5 Days | Suitability | 4.818 | 1.131 | 20.64 | 188.2 | Suitability | 4.816 | 1.132 | 20.54 | 185.8 | Suitability | 4.817 | 1.132 | 20.64 | 187.7 |
| Scattering Ray | Beginning | Suitability | 4.819 | 1.130 | 20.62 | 189.6 | Suitability | 4.821 | 1.130 | 20.52 | 189.8 | Suitability | 4.817 | 1.131 | 20.63 | 190.2 |
| | 5 Days | Suitability | 4.816 | 1.130 | 20.63 | 189.5 | Suitability | 4.820 | 1.132 | 20.51 | 188.6 | Suitability | 4.820 | 1.132 | 20.61 | 189.9 |
| | 10 Days | Suitability | 4.819 | 1.131 | 20.64 | 189.6 | Suitability | 4.818 | 1.131 | 20.53 | 189.2 | Suitability | 4.817 | 1.132 | 20.63 | 189.3 |
| | 20 Days | Suitability | 4.822 | 1.130 | 20.62 | 189.6 | Suitability | 4.817 | 1.133 | 20.54 | 187.7 | Suitability | 4.818 | 1.132 | 20.65 | 188.4 |
| | 30 Days | Suitability | 4.817 | 1.131 | 20.63 | 187.2 | Suitability | 4.819 | 1.132 | 20.57 | 187.3 | Suitability | 4.816 | 1.133 | 20.64 | 187.8 |

TABLE 3

| | | Lot No. | | | | | | | | | | | | | |
|---|---|---|---|---|---|---|---|---|---|---|---|---|---|---|---|
| | | SU-83001 | | | | | SU-83002 | | | | | SU-83003 | | | |
| | | | | | | | Remarks | | | | | | | | |
| Condition | Period | Result | pH | Density | Viscosity | Content | Result | pH | Density | Viscosity | Content | Result | pH | Density | Viscosity | Content |
| Long | Beginning | Suitability | 4.819 | 1.130 | 20.62 | 189.6 | Suitability | 4.821 | 1.130 | 20.51 | 189.8 | Suitability | 4.818 | 1.131 | 20.63 | 190.2 |

TABLE 3-continued

| | | Lot No. | | | | | | | | | | | | | |
|---|---|---|---|---|---|---|---|---|---|---|---|---|---|---|---|
| | | SU-83001 | | | | | SU-83002 | | | | | SU-83003 | | | |
| | | | | | | | Remarks | | | | | | | | |
| Condition | Period | Result | pH | Density | Viscosity | Content | Result | pH | Density | Viscosity | Content | Result | pH | Density | Viscosity | Content |
| Period | ning bility | | | | | | bility | | | | | bility | | | | |
| | 3 (Months) | Suitability | 4.819 | 1.131 | 20.63 | 189.9 | Suitability | 4.820 | 1.131 | 20.52 | 189.7 | Suitability | 4.818 | 1.132 | 20.62 | 190.2 |
| | 6 (Months) | Suitability | 4.818 | 1.129 | 20.62 | 188.4 | Suitability | 4.811 | 1.132 | 20.56 | 190.2 | Suitability | 4.821 | 1.131 | 20.61 | 188.6 |
| | 9 (Months) | Suitability | 4.821 | 1.131 | 20.65 | 190.1 | Suitability | 4.818 | 1.129 | 20.55 | 188.6 | Suitability | 4.821 | 1.130 | 20.64 | 188.9 |
| | 12 (Months) | Suitability | 4.818 | 1.129 | 20.65 | 188.5 | Suitability | 4.816 | 1.131 | 20.54 | 187.7 | Buitability | 4.818 | 1.132 | 20.64 | 186.5 |
| | 18 (Months) | Suitability | 4.817 | 1.133 | 20.64 | 187.7 | Suitability | 4.817 | 1.132 | 20.54 | 186.9 | Suitability | 4.819 | 1.133 | 20.56 | 187.4 |
| | 24 (Months) | Suitability | 4.818 | 1.131 | 20.65 | 186.0 | Suitability | 4.816 | 1.131 | 20.57 | 185.0 | Suitability | 4.816 | 1.132 | 20.67 | 185.8 |

EXPERIMENT 2

1. Procedure

This method was designed to evaluate activity based on the oral administration of the pharmaceutical liquid from the Example 1 to animals. The animals used in this test were male and female Sprague Dawley rats who were 7–8 weeks old and weighted 220+20 g, and male and female Day mice who were 6–7 weeks old and weighed 20+2.0 g and 18+2.0 g, respectively. Before performing this test, the animals were fed solid feed stuffs at a temperature of 24+2° C. and a moisture of 65+5%. 7 days prior to test initiation, the pharmaceutical liquid of the present invention was orally administrated to the animals. A group has 10 animals.

2. Results

The results obtained from the toxic activity test of the pharmaceutical liquid of the present invention are shown in Table 4 (Rats) and Table 5 (Mice) as follows:

In the Table 5, the mice that were treated with a 110 ml/kg dosage were killed. However, the mice treated with $LD_{50}$ at 109.6 ml/kg of average dosage lived.

Accordingly, the results from Tables 4 and 5 indicate suitable toxic activity with the pharmaceutical liquid of the present invention.

The invention being thus described, it will be obvious that the same may be varied in many ways. Such variations are not to be regarded as a departure from the spirit and scope of the invention, and all such modifications as would be obvious to one skilled in the art are intended to be included in the scope of the following claims.

What is claimed is:

1. A pharmaceutical liquid composition containing Bezoar Bovis, which comprises:
    Bezoar Bovis, Dioscoreae Rhizoma, Glycyrrhizae Radix, Ginseng Radix, Typhae Pollen, Massa Medicata Fermentata, Sojae Semen, Cinnamomi Cortex, Gelatin, Paeoniae Radix, Liriopis tuber, Scutellariae Radix, Angelicae Gigantis Radix, Ledebouriellae Radix, Atractylodis Rhizom Alba, Bupleuri Radix, Platycodi Radix, Armeniacae Semen, Hoelen, Cnidii Rhizoma,

TABLE 4

| Sex | Dosage (ml/kg) | 1 (Day) | 2 (Days) | 3 (Days) | 4 (Days) | 5 (Days) | 6 (Days) | 7 (Days) | Fetal % | $ID_{50}$ |
|---|---|---|---|---|---|---|---|---|---|---|
| Male | 15 | 0/10 | | | | | | 0/10 | | |
| | 30 | " | | | | | | | | |
| | 45 | " | | | | | | | | |
| | 60 | " | | | | | | | | |
| | 75 | " | | | | 1/10 | | 1/10 | 10 | |
| Female | 15 | 0/10 | | | | | | 0/10 | | |
| | 30 | " | | | | | | " | | |
| | 45 | " | | | | | | " | | |
| | 60 | " | | | | | | " | | |
| | 75 | " | | | | | | " | | |

TABLE 5

| Sex | Dosage (ml/Kg) | 1 (Day) | 2 (Days) | 3 (Days) | 4 (Days) | 5 (Days) | 6 (Days) | 7 (Days) | Fetal % | $ID_{50}$ |
|---|---|---|---|---|---|---|---|---|---|---|
| Male | 70 | 0/10 | | | | 2/10 | | 2/10 | 20 | |
| | 80 | " | | | | 2/10 | | 3/10 | 30 | |
| | 90 | " | 1/10 | | 2/10 | | | 5/10 | 50 | |
| | 100 | " | 3/10 | 5/10 | | 7/10 | | 8/10 | 80 | |
| | 110 | " | 2/10 | 4/10 | 5/10 | 7/10 | 10/10 | 10/10 | 100 | 109.6 |
| Female | 70 | 0/10 | | | | | | | 0 | |
| | 80 | " | | | 1/10 | | 2/10 | 2/10 | 20 | |
| | 90 | " | | 2/10 | | 4/10 | | 4/10 | 40 | |
| | 100 | " | 2/10 | 4/10 | 7/10 | | 8/10 | 8/10 | 80 | |
| | 110 | " | 3/10 | 5/10 | 8/10 | 9/10 | | 10/10 | 100 | 109.6 |

*Antellopis Cornu*, Moschus, Borneol, *Ampelopsis Radix*, and *Zingiberis Rhizoma*.

2. The pharmaceutical liquid composition of claim 1, wherein said *Bezoar Bovis* is *Bos taurus* var. *domesticus Gmelin*.

3. The pharmaceutical liquid composition of claim 1, wherein said *Bezoar Bovis* is present in an amount of 45 parts by weight, *Dioscoreae Rhizoma* is present in an amount of 263 parts, *Glycyrrhizae Radix* is present in an amount of 188 parts, *Ginseng Radix* is present in an amount of 94 parts, *Typhae Pollen* is present in an amount of 94 parts, *Massa Medicata Fermentata* is present in an amount of 94 parts, *Sojae germinatum Semen* is present in an amount of 66 parts, *Cinnamomi Cortex* is present in an amount of 66 parts, Gelatin is present in an amount of 66 parts, *Paeoniae Radix* is present in an amount of 56 parts, *Liriopis Tuber* is present in an amount of 56 parts, *Scutellariae Radix* is present in an amount of 56 parts, *Angelicae Gigantis Radix* is present in an amount of 56 parts, *Ledebouriellae Radix* is present in an amount of 56 parts, *Atractylodis Rhizoma Alba* is present in an amount of 56 parts, *Bupleuri Radix* is present in an amount of 47 parts, *platycodi Radix* is present in an amount of 47 parts, *Armeniacae Semen* is present in an amount of 47 parts, Hoelen is present in an amount of 47 parts, *Cnidii Rhizoma* is present in an amount of 47 parts, *Antellopis Cornu* is present in an amount of 38 parts, Moschus is present in an amount of 38 parts, Borneol is present in an amount of 38 parts, *Ampelopsis Radix* is present in an amount of 28 parts, and *Zingiberis Rhizoma* is present in an amount of 28 parts, by weight.

4. The pharmaceutical liquid composition of claim 1, further comprising an aromatic agent, sweetening agent, emulsifier, colloidal agent, suspension agent, and preservative.

5. The pharmaceutical liquid composition of claim 1, wherein said pharmaceutical liquid composition is a suspension form.

6. The pharmaceutical liquid composition of claim 1, wherein said pharmaceutical liquid composition is a gel form.

* * * * *

(12) REEXAMINATION CERTIFICATE (4347th)
United States Patent
Kim

(10) Number: US 5,225,203 C1
(45) Certificate Issued: May 15, 2001

(54) PHARMACEUTICAL LIQUID COMPOSITION CONTAINING BEZOAR BOVIS

(75) Inventor: Young S. Kim, Seoul (KR)

(73) Assignee: Won Kyu (Son) Kim, Seoul (KR)

Reexamination Request:
No. 90/005,404, Jun. 24, 1999

Reexamination Certificate for:
Patent No.: 5,225,203
Issued: Jul. 6, 1993
Appl. No.: 07/878,215
Filed: May 4, 1992

Related U.S. Application Data

(63) Continuation-in-part of application No. 07/595,671, filed on Oct. 11, 1990, now Pat. No. 5,133,964, which is a continuation of application No. 07/171,432, filed on Mar. 21, 1988, now abandoned.

(30) Foreign Application Priority Data

Jul. 1, 1987 (KR) .................................................. 87-6998

(51) Int. Cl.$^7$ .................................................. A61K 35/78
(52) U.S. Cl. .................. 424/195.1; 424/520; 424/551
(58) Field of Search ............................. 424/195.1, 537, 424/551

(56) References Cited

U.S. PATENT DOCUMENTS

| | | |
|---|---|---|
| 4,535,075 | 8/1985 | Kurono . |
| 4,543,355 | 9/1985 | Ishizumi . |
| 4,567,164 | 1/1986 | Shimada . |
| 4,587,262 | 5/1986 | Arnould . |
| 4,598,089 | 7/1986 | Hadvary . |
| 5,133,964 | 7/1992 | Kim . |

OTHER PUBLICATIONS

Results of Revaluation of Medical Effect, 3$^{rd}$ Part (1985–86).
Collection of Thesis of Doctor's and Master's Degree in Oriental Medicine, 4$^{th}$ Ed., 250 (1977).
Korea Pharmacopeia, 5$^{th}$ Revision, vol. 2, p. 581 (1987).

*Primary Examiner*—Jean C Witz

(57) ABSTRACT

A pharmaceutical liquid composition such as suspension, gel, or sol preparation, contains Bezoar Bovis, Dioscoreae Rhizoma, Glycyrrhizae Radix, Ginseng Radix, Typhae Pollen, Massa Medicata Fermentata, Sojae germinatum Semen, Cinnamomi Cortex, Gelatin, Paeoniae Radix Liriopis Tuber, Scutellariae Radix, Angelicae Gigantis Radix, Ledebouriellae Radix, Atractylodis Rhizoma Alba, Bupleuri Radix, Platycodi Radix, Armeniacae Semen, Hoelen, Cnidii Rhizoma, Antellopis Cornu, Moschus, Borneol, Ampelopsis Radix, and Zingiberis Rhizoma for easy oral and parental administration thereof to critical patients.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claim 1 is determined to be patentable as amended.

Claims 2–6, dependent on an amended claim, are determined to be patentable.

1. A pharmecutical liquid composition containing Bezoar Bovis, which comprises:

Bezoar Bovis, Dioscoreae Rhizoma, Glycyrrhizae Radix, Ginseng Radix, Typhae Pollen, Massa Medicata Fermentata, Sojae Semen, Cinnamomi Cortex, Gelatin, Paeoniae Radix, Liriopis tuber, Scutellariae Radix, Angelicae Gigantis Radix, Ledebouriellae Radix, Atractylodis Rhizom Alba, Bupleuri Radix, Platycodi Radix, Armeniacae Semen, Hoelen, Cnidii Rhizoma, Antellopis Cornu, Moschus, Borneol, Ampelopsis Radix, and Zingiberis Rhizoma;

*wherein the components are present as a microparticle solution, water extract or alcohol extract.*

\* \* \* \* \*